United States Patent
Bergmann

(10) Patent No.: US 8,853,614 B2
(45) Date of Patent: Oct. 7, 2014

(54) METHOD FOR CALIBRATING AT LEAST ONE DETECTOR ARRAY FORMED BY A PLURALITY OF DETECTORS

(75) Inventor: Bernd Bergmann, Wedemark (DE)

(73) Assignee: Fagus-Grecon Greten GmbH & Co. KG, Alfeld (DE)

( * ) Notice: Subject to any disclaimer, the term of this patent is extended or adjusted under 35 U.S.C. 154(b) by 161 days.

(21) Appl. No.: 13/422,640

(22) Filed: Mar. 16, 2012

(65) Prior Publication Data

US 2012/0248323 A1      Oct. 4, 2012

(30) Foreign Application Priority Data

Mar. 16, 2011   (DE) .......................... 10 2011 014 103

(51) Int. Cl.
  *G01T 1/29*    (2006.01)
  *G01N 23/083*  (2006.01)
  *A61B 6/00*    (2006.01)

(52) U.S. Cl.
  CPC ........ *G01N 23/083* (2013.01); *G01N 2223/619* (2013.01); *G01N 2223/3035* (2013.01); *A61B 6/585* (2013.01)
  USPC ...................................................... 250/252.1

(58) Field of Classification Search
  CPC ..... A61B 6/585; G01N 23/06; G01N 23/083; G01N 2223/303; G01N 2223/3035; G01N 2223/619; G01T 7/005
  USPC ....................................................... 250/252.1
  See application file for complete search history.

(56) References Cited

U.S. PATENT DOCUMENTS

| 4,352,020 A | 9/1982 | Horiba et al. |
| 5,506,880 A * | 4/1996 | Scardino et al. ............. 378/98.2 |
| 6,148,057 A | 11/2000 | Urchuk et al. |

OTHER PUBLICATIONS

Mass attenuation coefficient, Wikipedia, Apr. 28, 2010, 2 pages.

* cited by examiner

*Primary Examiner* — Constantine Hannaher
(74) *Attorney, Agent, or Firm* — Muncy, Geissler, Olds & Lowe, P.C.

(57) ABSTRACT

In a method for calibrating at least one detector array formed by a plurality of detectors that is exposed to a high-energy, fan-shaped expanding radiation emanating from an approximately point-like energy source, serving the penetration of a material for measuring physical properties due to the absorption capacity of the material, it is provided that at least two in each case homogeneously formed calibration bodies whose gradually differing absorption is designed in a way that the absorption capacity of the one calibration body is lower and the one of the other calibration body is higher than the absorbance capacity of the material to be measured.

4 Claims, 2 Drawing Sheets

METHOD FOR CALIBRATING AT LEAST ONE DETECTOR ARRAY FORMED BY A PLURALITY OF DETECTORS

BACKGROUND OF THE INVENTION

1. Field of the Invention

The invention relates to a method for calibrating at least one detector array formed by a plurality of detectors that is exposed to a high-energy, fan-shaped widening radiation emanating from an approximately point-like energy source.

When penetrating a material, the radiation interacts therewith enabling the determination physical properties of the material.

In the production of various materials or during their processing they are penetrated by X-ray sources to determine physical properties of the material. Such physical properties include for example the mass per unit area, the density or the thickness of a, for example, plate-like material, especially in the wood products industry.

2. Brief Discussion of the Related Art

The detectors used for the gauging of materials are often detector arrays, which are composed of a plurality of individual detector elements. The individual detector elements have a transmission behavior that is independent from one another. In addition, from the point-like radiation source there are different path lengths for the fan-shaped expanding radiation on the way to the individual detector elements of the detector array.

Often the detector array length is greater than the material to be measured. In this case the measurement must meet the requirement that the same test result is obtained, regardless of what specific area of the detector array is covered by the material.

Because of these influences on the individual detectors, regular calibration of the detectors is required.

BRIEF DISCUSSION OF THE DRAWINGS

Figure 1:
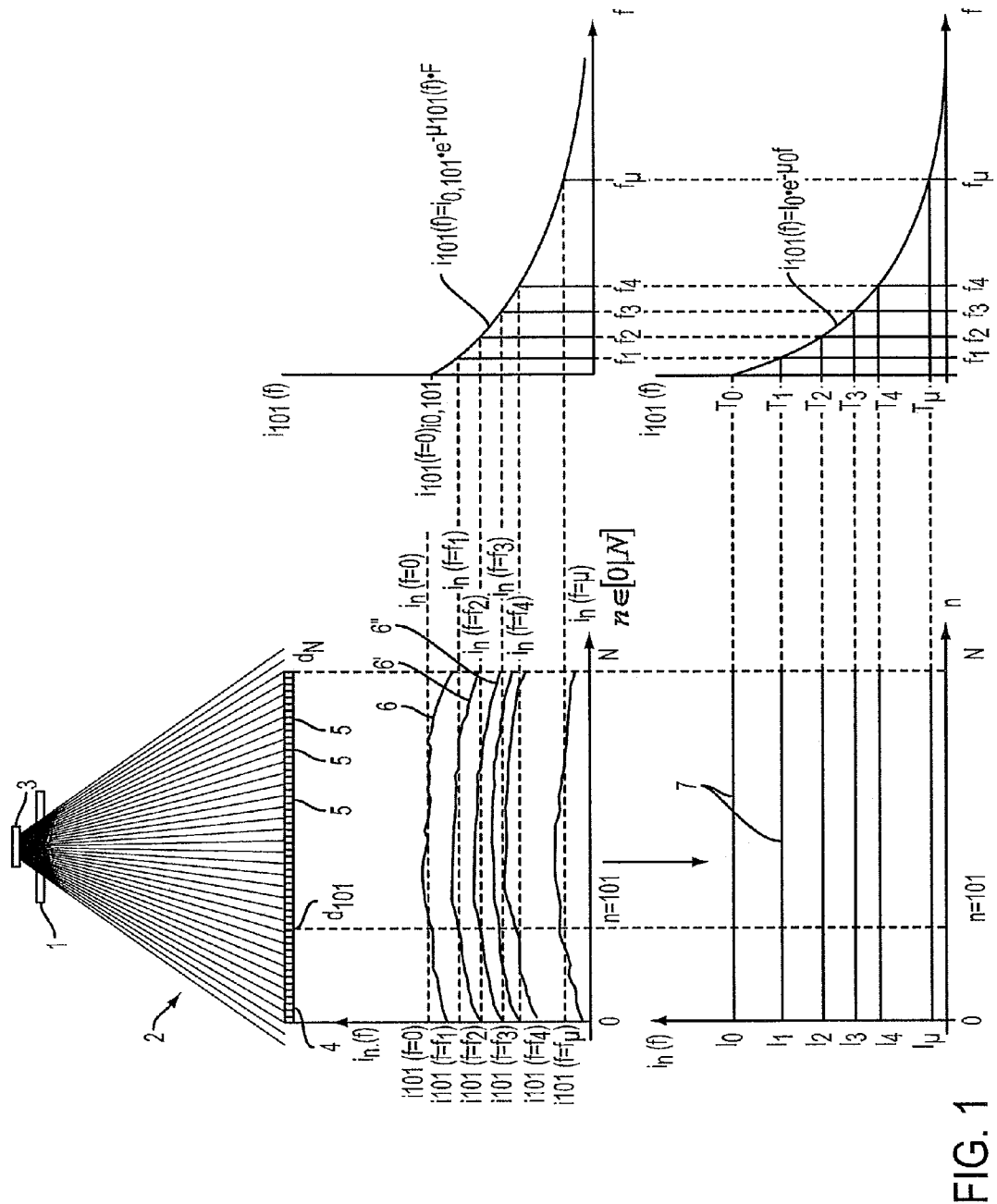
Figure 2:
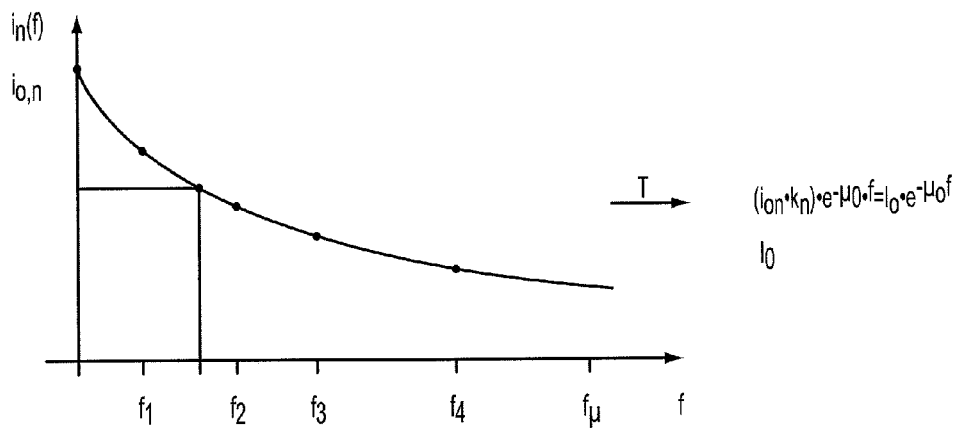
Figure 3:
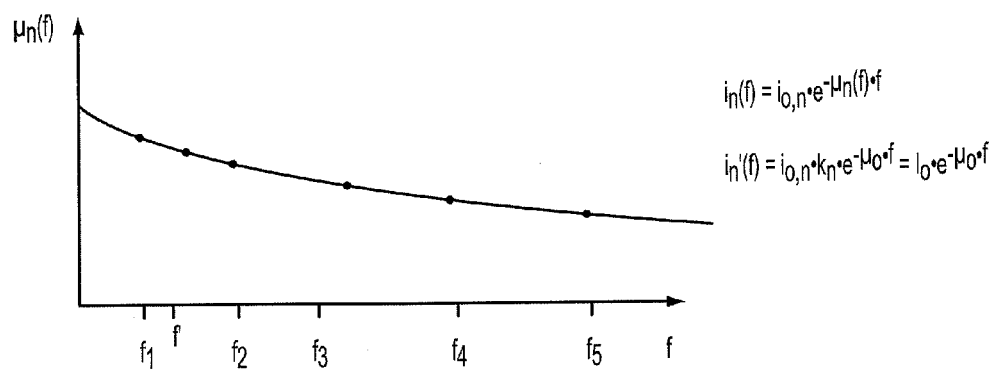

FIG. 1 shows a side view of an experimental setup for the method according to the invention; and FIGS. 2 and 3 show an example of the profile of Formula (1).

SUMMARY OF THE INVENTION

It is the object of the invention to provide a simple and speedy method of calibrating.

According to the invention this object is achieved in that at least two in each case homogeneously formed calibration bodies whose gradually differing absorption is designed in a way that the absorption capacity of the one calibration body is lower and the one of the other calibration body is higher than the absorbance capacity of the material to be measured, are successively entered into the beam path, and that for each detector element in the detector array and for each calibration body the absorption capacity, i.e., the intensity of the radiation, is measured, and the absorbance capacity of each calibration body is assigned to a known property of these calibration bodies and that the absorption capacity is interpolated in sections between these known properties.

In the method of the invention, a calibration is not performed with a sample of the material which is to be irradiated subsequently. Instead, calibration bodies, whose absorption is similar to the absorption of the material to be irradiated, are used. According to the invention, these calibration bodies are formed homogeneously, therefore the calibration bodies differ from inhomogeneous materials such as wood or rayon.

The absorption capacity of each calibration body is measured. For the calculation of an absorption capacity of the material the individual measured values are then used in such a way that the absorption capacity of the individual calibration bodies is assigned to a known property, such as the mass per unit area, of these calibration bodies, and that the absorption capacity is interpolated in sections between the known properties such as mass by unit area. Thus, by measuring a few calibration bodies, an absorption capacity of the material to be measured may be determined, according to which the individual detector elements are then normalized in the calibration.

DETAILED DISCUSSION OF THE PREFERRED EMBODIMENTS

A first embodiment of the invention provides for four to eight calibration bodies to be used. This number of calibration bodies can cover a specific area of a physical property, such as different masses per unit area or different thicknesses. Each calibration body is formed homogeneously so that it reflects the material to be measured as such. The calibration bodies are formed for example from glass, plastic or metal, thus, for the gauging of wood a plastic or a plexiglass may be used.

According to an embodiment of the invention, when calibrating, a full-irradiation without calibration bodies is performed. This full-irradiation shows the maximum intensity of the radiation that can impinge on the detector elements. According to an embodiment, the full-irradiation is used in that initially an interpolation of the absorption coefficient V over the mass per unit area f is performed for an interpolation of the absorption capacity or intensity. The intensity then has the form of an e-function. Thus, the intensity of a detector element $d_n$ may be described as follows:

$$i_n(f) = i_{0,n} \cdot e^{-\mu_n(f) \cdot f} \quad n \in [0|N]$$

From this intensity function a transformation to an e-function with a constant absorption coefficient $\mu_0$ is performed. The result is therefore an intensity function, such that for the detector elements $d_n$ the following applies:

$$i_n(f) = i_{0,n} \cdot e^{-\mu_n(f) \cdot f} \xrightarrow{T} i_n^*(f) = i_{0,n} \cdot k_n \cdot e^{-\mu_0 \cdot f} = I_0 \cdot e^{-\mu_0 \cdot f} = i(f)$$

From the measurement of homogeneous calibration bodies $K_i$ with a constant density and a known mass per unit area $f_i$ follows:

$$K_1, K_2, K_3, \ldots, K_M \text{ with } \rho_1 = \rho_2 = \rho_3 = \ldots = \rho_M \text{ and} \quad (1)$$

$$f_1 < f_2 < f_{m-1} < f_m < \ldots < f_M$$

$$i_n(f_i) = i_{0,n} e^{-\mu_n(f_i) f_i} \text{ where } n \in [0|N] \wedge i \in [1|M]$$

$$\mu_n(f_i) = \mu_{n,i} \text{ discrete values}$$

$$\Rightarrow i_n(f_i) = i_{0,n} e^{-\mu_{n,i} \cdot f_i} = i_{n,i} \Rightarrow \mu_{n,i} = \frac{1}{f_i} \ln\left(\frac{i_{0,n}}{i_{n,i}}\right)$$

An example of the profile of (1) is given in FIGS. 2 and 3.

The drawing illustrated an exemplary embodiment of the invention, resulting in further inventive features. FIG. 1 shows a side view of an experimental setup for the method according to the invention, which is assigned a graphic for the absorption by means of the elements of a detector array and a graphic for a transformed representation of the intensity of the individual detector elements.

In the method according to the invention different calibration bodies 1 are entered into the beam path of a pointlike X-ray source 3. The rays of the X-ray source impinge in a fan-like expanding beam path 2 onto a detector array 4. The detector array 4 is formed from a plurality of detectors 5.

The drawing illustrates the intensity curves 6, 6', 6" for individual calibration bodies 1 across all the detector elements 5. Since in the beam path for the detector elements 5 arranged at the outer ends of the detector array 4 a longer beam path is required, the intensity in these areas decreases.

According to the invention a transformation of an e-function with a constant absorption coefficient $\mu_0$ is carried out with the measured absorbance capacity or intensities. If f=0, the e-function=1. As a result, the horizontal lines 7 shown in the drawing are obtained for each of the various calibration bodies across the entire detector array 4.

The resulting normalized values may be entered into a table, which may be used later by the users of the high-energy power source and the detector array 4.

The drawing of the experimental setup and the four graphs shows the processing of data at a detector location $d_{101}$. In the upper right representation the intensities obtained for distinct specimens 1 are first normalized to known absorption coefficient $d_{101}$. The individual specimens 1 correspond to sampling points $f_1, f_2, f_3$, the function between these sampling points are interpolated. The lower right representation shows the transformation of this intensity function of $d_{101}$ to a constant absorption coefficient $\mu_0$. This then results in the lower left representation with normalized intensities across all the detector elements 5.

The invention claimed is:

1. A method for calibrating at least one detector array formed by a plurality of detectors that is exposed to a high energy, fan-shaped expanding radiation emanating from an approximately point-like energy source, serving the penetration of a material for measuring physical properties due to the absorption capacity of the material, comprising the steps of:

entering successively at least two in each case homogeneously formed calibration bodies whose gradually differing absorption is designed in a way that the absorption capacity of the one calibration body is lower and the one of the other calibration body is higher than the absorption capacity of the material to be measured, into the beam path, measuring for each detector element in the detector array and for each calibration body the absorption capacity, i.e., the intensity of the radiation, assigning the absorption capacity of each calibration body to a known mass per unit area property of these calibration bodies, and interpolating the absorption capacity in mass per unit area sections between these known mass per unit area properties;

wherein:

initially, before the steps using calibration bodies, an interpolation of the absorption coefficient over the mass per unit area with full-irradiation is carried out for an interpolation of the intensity, and for each detector element the intensity is transformed to an e-function with constant $u_0$.

2. The method according to claim 1, wherein four to eight calibration bodies are used.

3. The method according to claim 1, wherein calibration bodies with known mass per unit area are used.

4. The method according to claim 1, wherein calibration bodies made of glass, plastic or metal are used.

* * * * *